United States Patent
Wasserman et al.

(10) Patent No.: US 11,471,676 B2
(45) Date of Patent: Oct. 18, 2022

(54) DELIVERING TUMOR TREATING FIELDS (TTFIELDS) USING IMPLANTABLE TRANSDUCER ARRAYS

(71) Applicant: Novocure GmbH, Root (CH)

(72) Inventors: Yoram Wasserman, Haifa (IL); Zeev Bomzon, Kiryat Tivon (IL); Hadas Sara Hershkovich, Kiryat Motzkin (IL); Ariel Naveh, Haifa (IL); Moshe Giladi, Moshav Herut (IL); Eilon Kirson, Ramat Hasharon (IL); Golan Bar-Tal, Zichron Ya'akov (IL); Tali Voloshin-Sela, Kibbutz Gvat (IL)

(73) Assignee: Novocure GmbH, Root (CH)

( * ) Notice: Subject to any disclaimer, the term of this patent is extended or adjusted under 35 U.S.C. 154(b) by 0 days.

(21) Appl. No.: 16/801,972

(22) Filed: Feb. 26, 2020

(65) Prior Publication Data
US 2020/0269043 A1    Aug. 27, 2020

Related U.S. Application Data

(60) Provisional application No. 62/811,311, filed on Feb. 27, 2019.

(51) Int. Cl.
*A61N 1/05* (2006.01)
*A61N 1/36* (2006.01)
*A61N 1/378* (2006.01)

(52) U.S. Cl.
CPC ........... *A61N 1/36002* (2017.08); *A61N 1/05* (2013.01); *A61N 1/3787* (2013.01)

(58) Field of Classification Search
CPC ..... A61N 1/36002; A61N 1/05; A61N 1/3787
See application file for complete search history.

(56) References Cited

U.S. PATENT DOCUMENTS

| | | | |
|---|---|---|---|
| 6,868,289 | B2 | 3/2005 | Palti |
| 7,016,725 | B2 | 3/2006 | Palti |
| 7,089,054 | B2 | 8/2006 | Palti |
| 7,136,699 | B2 | 11/2006 | Palti |
| 7,333,852 | B2 | 2/2008 | Palti |
| 7,467,011 | B2 | 12/2008 | Palti |
| 7,519,420 | B2 | 4/2009 | Palti |
| 7,565,205 | B2 | 7/2009 | Palti |

(Continued)

FOREIGN PATENT DOCUMENTS

WO      2002047565 A2    6/2002

OTHER PUBLICATIONS

International Search Report and Written Opinion issued in application No. PCT/IB2020/051660 dated Jul. 22, 2020.

*Primary Examiner* — Ankit D Tejani
*Assistant Examiner* — Joshua Brendon Solomon
(74) *Attorney, Agent, or Firm* — Potomac Law Group, PLLC

(57) ABSTRACT

Tumor treating fields (TTFields) can be delivered by implanting a plurality of sets of implantable electrode elements within a person's body. Temperature sensors positioned to measure the temperature at the electrode elements are also implanted, along with a circuit that collects temperature measurements from the temperature sensors. In some embodiments, an AC voltage generator configured to apply an AC voltage across the plurality of sets of electrode elements is also implanted within the person's body.

22 Claims, 8 Drawing Sheets

(56) References Cited

U.S. PATENT DOCUMENTS

| | | | |
|---|---|---|---|
| 7,565,206 B2 | 7/2009 | Palti | |
| 7,599,745 B2 | 10/2009 | Palti | |
| 7,599,746 B2 | 10/2009 | Palti | |
| 7,706,890 B2 | 4/2010 | Palti | |
| 7,715,921 B2 | 5/2010 | Palti | |
| 7,805,201 B2 | 9/2010 | Palti | |
| 7,890,183 B2 | 2/2011 | Palti et al. | |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,170,684 B2 | 5/2012 | Palti | |
| 8,175,698 B2 | 5/2012 | Palti et al. | |
| 8,229,555 B2 | 7/2012 | Palti | |
| RE43,618 E | 8/2012 | Palti | |
| 8,244,345 B2 | 8/2012 | Palti | |
| 8,406,870 B2 | 3/2013 | Palti | |
| 8,447,395 B2 | 5/2013 | Palti et al. | |
| 8,447,396 B2 | 5/2013 | Palti et al. | |
| 8,465,533 B2 | 6/2013 | Palti | |
| 8,706,261 B2 | 4/2014 | Palti | |
| 8,715,203 B2 | 5/2014 | Palti | |
| 8,718,756 B2 | 5/2014 | Palti | |
| 8,764,675 B2 | 7/2014 | Palti | |
| 9,023,090 B2 | 5/2015 | Palti | |
| 9,023,091 B2 | 5/2015 | Palti | |
| 9,039,674 B2 | 5/2015 | Palti et al. | |
| 9,056,203 B2 | 6/2015 | Palti et al. | |
| 9,440,068 B2 | 9/2016 | Palti et al. | |
| 9,655,669 B2 | 5/2017 | Palti et al. | |
| 9,750,934 B2 | 9/2017 | Palti et al. | |
| 9,910,453 B2 | 3/2018 | Wasserman et al. | |
| 10,188,851 B2 | 1/2019 | Wenger et al. | |
| 10,441,776 B2 | 10/2019 | Kirson et al. | |
| 2005/0222646 A1* | 10/2005 | Kroll | A61N 1/326 607/72 |
| 2006/0167499 A1 | 7/2006 | Palti | |
| 2007/0225766 A1 | 9/2007 | Palti | |
| 2007/0239213 A1 | 10/2007 | Palti | |
| 2008/0033492 A1* | 2/2008 | Siff | A61N 1/36021 607/3 |
| 2009/0076366 A1 | 3/2009 | Palti | |
| 2012/0283726 A1 | 11/2012 | Palti | |
| 2014/0276754 A1* | 9/2014 | Gilbert | H02M 7/53871 606/33 |
| 2014/0330268 A1 | 11/2014 | Palti et al. | |
| 2017/0120041 A1 | 5/2017 | Wenger et al. | |
| 2017/0215939 A1 | 8/2017 | Palti et al. | |
| 2017/0281934 A1* | 10/2017 | Giladi | A61N 1/40 |
| 2018/0001075 A1 | 1/2018 | Kirson et al. | |
| 2018/0008708 A1 | 1/2018 | Giladi et al. | |
| 2018/0050200 A1* | 2/2018 | Wasserman | A61N 1/0408 |
| 2018/0160933 A1 | 6/2018 | Urman et al. | |
| 2018/0202991 A1 | 7/2018 | Giladi et al. | |
| 2019/0117956 A1 | 4/2019 | Wenger et al. | |
| 2019/0117963 A1 | 4/2019 | Travers et al. | |
| 2019/0117969 A1 | 4/2019 | Schmidt et al. | |
| 2019/0117970 A1 | 4/2019 | Schmidt et al. | |
| 2019/0117971 A1 | 4/2019 | Schmidt et al. | |
| 2019/0117972 A1 | 4/2019 | Schmidt et al. | |
| 2019/0117973 A1 | 4/2019 | Schmidt et al. | |
| 2019/0307781 A1 | 10/2019 | Krex et al. | |
| 2019/0308016 A1 | 10/2019 | Wenger et al. | |
| 2020/0001069 A1 | 1/2020 | Kirson et al. | |
| 2020/0009376 A1 | 1/2020 | Chang et al. | |
| 2020/0009377 A1 | 1/2020 | Chang et al. | |
| 2020/0016067 A1 | 1/2020 | Gotlib et al. | |
| 2020/0023179 A1 | 1/2020 | Bomzon et al. | |
| 2020/0061360 A1 | 2/2020 | Hagemann et al. | |
| 2020/0061361 A1 | 2/2020 | Hagemann et al. | |
| 2020/0069937 A1 | 3/2020 | Naveh et al. | |
| 2020/0078582 A1 | 3/2020 | Alon et al. | |
| 2020/0108031 A1 | 4/2020 | Borst et al. | |
| 2020/0121728 A1 | 4/2020 | Wardak et al. | |
| 2020/0129761 A1 | 4/2020 | Bomzon et al. | |
| 2020/0146586 A1 | 5/2020 | Naveh et al. | |
| 2020/0155835 A1 | 5/2020 | Wasserman et al. | |
| 2020/0171297 A1 | 6/2020 | Kirson et al. | |
| 2020/0179512 A1 | 6/2020 | Giladi et al. | |
| 2020/0219261 A1 | 7/2020 | Shamir et al. | |
| 2020/0330756 A1 | 10/2020 | Schmidt et al. | |
| 2020/0330757 A1 | 10/2020 | Schmidt et al. | |
| 2020/0330758 A1 | 10/2020 | Schmidt et al. | |
| 2020/0338344 A1 | 10/2020 | Schmidt et al. | |
| 2020/0338345 A1 | 10/2020 | Schmidt et al. | |
| 2020/0338346 A1 | 10/2020 | Schmidt et al. | |

* cited by examiner

DELIVERING TUMOR TREATING FIELDS (TTFIELDS) USING IMPLANTABLE TRANSDUCER ARRAYS

CROSS REFERENCE TO RELATED APPLICATIONS

This Application claims the benefit of U.S. Provisional Application 62/811,311, filed Feb. 27, 2019, which is incorporated herein by reference in its entirety.

BACKGROUND

TTFields (Tumor Treating Fields) therapy is a proven approach for treating tumors. Referring to FIG. 1, in the prior art Optune® system for delivering TTFields, the TTFields are delivered to patients via four transducer arrays placed on the patient's skin in close proximity to a tumor. The transducer arrays are arranged in two pairs. One of those pairs (A/A) is positioned on the left and right sides of the head; and the other one of those pairs (B/B) is positioned on the front and back of the head. Each transducer array is connected via a multi-wire cable to an AC voltage generator. The AC voltage generator (a) sends an AC current through one pair of arrays during a first period of time; then (b) sends an AC current through the other pair of arrays during a second period of time; then repeats steps (a) and (b) for the duration of the treatment.

Each transducer array is configured as a set of capacitively coupled electrode elements (about 2 cm in diameter) that are interconnected via flex wires. Each electrode element includes a ceramic disk that is sandwiched between a layer of an electrically conductive medical gel and an adhesive tape. When placing the arrays on the patient, the medical gel adheres to the contours of the patient's skin and ensures good electric contact of the device with the body. The adhesive tape holds the entire array in place on the patient as the patient goes about their daily activities.

The amplitude of the alternating current that is delivered via the transducer arrays is controlled so that skin temperature (as measured on the skin below the transducer arrays) does not exceed a safety threshold of 41° C. The temperature measurements on the patient's skin are obtained using thermistors placed beneath some of the disks of the transducer arrays. In the existing Optune® system, each array includes 8 thermistors, with one thermistor positioned beneath a respective disk in the array. (Note that most arrays include more than 8 disks, in which case the temperature measurements are only performed beneath a sub-set of the disks within the array).

The thermistors in each of the four arrays are connected via long wires to an electronic device called the "cable box" where the temperature from all 32 thermistors (4 arrays×8 thermistors per array A, A, B, B) is measured and analog-to-digital converted into digital values for each thermistor. These measurements are then transmitted from the cable box to the AC voltage generator via an additional two wires that facilitate two-way digital serial communications between the cable box and the AC voltage generator. The controller in the AC voltage generator uses the temperature measurements to control the current to be delivered via each pair of arrays A, A, B, B in order to maintain temperatures below 41° C. on the patient's skin. The current itself is delivered to each array via an additional wire (i.e., one wire for each array) that runs from the AC voltage generator through the cable box to the array.

In the existing Optune® system there are four long 10-wire cables (each of which runs between a respective array and the cable box) and one 8-wire spiral cord that runs between the AC voltage generator and the cable box. Each of the 10-wire cables has 8 wires for carrying signals from the 8 thermistors, 1 wire for the common of all 8 thermistors, plus 1 wire for providing the TTFields signal to the array. The 8-wire spiral cord has 1 wire for power to the cable box (Vcc), 1 wire for ground to the cable box, 2 wires for data communication (to send the temperature readings to the AC voltage generator), plus 4 wires for the TTFields signals (i.e., one for each of the four arrays).

SUMMARY OF THE INVENTION

One aspect of the invention is directed to a first apparatus for delivering tumor treating fields. The first apparatus comprises a plurality of sets of electrode elements, and each of the sets of electrode elements is configured for implantation within a person's body. The first apparatus also comprises a plurality of temperature sensors configured for implantation within the person's body and positioned with respect to the sets of electrode elements to measure a temperature at each of the sets of electrode elements. The first apparatus also comprises a circuit configured for implantation within the person's body configured for collecting temperature measurements from the plurality of temperature sensors. And the first apparatus also comprises an AC voltage generator configured for implantation within the person's body and configured to apply an AC voltage across the plurality of sets of electrode elements.

Some embodiments of the first apparatus further comprise an inductively coupled circuit configured for implantation within the person's body and configured to power the AC voltage generator.

Some embodiments of the first apparatus further comprise a battery configured for implantation within the person's body and configured to power the AC voltage generator. Optionally, these embodiments may further comprise an inductively coupled circuit configured for implantation within the person's body and configured to charge the battery.

In some embodiments of the first apparatus, each of the sets of electrode elements comprises a plurality of capacitively coupled electrode elements. Optionally, in these embodiments, each of the capacitively coupled electrode elements comprises a ceramic disc.

In some embodiments of the first apparatus, each of the temperature sensors comprises a thermistor. In some embodiments of the first apparatus, the plurality of sets of electrode elements, the plurality of temperature sensors, the circuit, and the AC voltage generator are all implanted in the person's body.

Another aspect of the invention is directed to a second apparatus for delivering tumor treating fields. The second apparatus comprises a plurality of sets of electrode elements, and each of the sets of electrode elements is configured for implantation within a person's body. The second apparatus also comprises a plurality of temperature sensors configured for implantation within the person's body and positioned to measure a temperature at each of the sets of electrode elements. And the second apparatus also comprises a circuit configured for implantation within the person's body configured for collecting temperature measurements from the plurality of temperature sensors.

In some embodiments of the second apparatus, each of the sets of electrode elements comprises a plurality of capacitively coupled electrode elements. In some embodiments of the second apparatus, each of the temperature sensors comprises a thermistor. In some embodiments of the second apparatus, the plurality of sets of electrode elements, the plurality of temperature sensors, and the circuit are all implanted in the person's body.

Another aspect of the invention is directed to a third apparatus for delivering tumor treating fields. The third apparatus comprises a plurality of sets of electrode elements, and each of the sets of electrode elements is configured for implantation within a person's body. The third apparatus also comprises a plurality of temperature sensors configured for implantation within the person's body and positioned to measure a temperature at each of the sets of electrode elements, And the third apparatus also comprises an AC voltage generator configured for implantation within the person's body and configured to apply an AC voltage across the plurality of sets of electrode elements.

Some embodiments of the third apparatus further comprise an inductively coupled circuit configured for implantation within the person's body and configured to power the AC voltage generator.

Some embodiments of the third apparatus further comprise a battery configured for implantation within the person's body and configured to power the AC voltage generator. Optionally, these embodiments may further comprise an inductively coupled circuit configured for implantation within the person's body and configured to charge the battery.

In some embodiments of the third apparatus, each of the sets of electrode elements comprises a plurality of capacitively coupled electrode elements. Optionally, in these embodiments, each of the capacitively coupled electrode elements may comprise a ceramic disc.

In some embodiments of the third apparatus, each of the temperature sensors comprises a thermistor. In some embodiments of the third apparatus, the plurality of sets of electrode elements, the plurality of temperature sensors, and the AC voltage generator are all implanted in the person's body.

BRIEF DESCRIPTION OF THE DRAWINGS

Various embodiments are described in detail below with reference to the accompanying drawings, wherein like reference numerals represent like elements, and wherein dotted lines represent implanted components.

DESCRIPTION OF THE PREFERRED EMBODIMENTS

Instead of using transducer arrays positioned on the patient's skin to deliver TTFields (as in the FIG. 1 embodiment described above), the embodiments described herein use transducer arrays that are implanted within a patient's body to deliver TTFields. Implanting the transducer arrays can provide a number of potential advantages. These potential advantages include (1) hiding of the arrays from people with whom the patient interacts; (2) improving patient comfort (by avoiding the skin irritation, sensations of heating, and/or limitations on motion that can result from arrays that are positioned on the patient's skin); (3) improving electrical contact between the transducer arrays and the patient's body; (4) eliminating the need for shaving regions on which the arrays are placed (as hair growth can interfere with the delivery of TTFields); (5) avoiding the risk that detachment of the transducer arrays will interrupt the delivery of TTFields; (6) significantly reducing the power required to deliver TTFields (e.g., by reducing the physical distance between the transducer arrays and the tumor and bypassing anatomical structures that have high resistivity, e.g., the skull); (7) significantly reducing the weight of the device that must be carried by the patient (e.g., by using smaller batteries to take advantage of the reduced power requirements); (8) avoiding the skin irritation that can occur when transducer arrays are positioned on the patient's skin; and (9) making it possible to deliver TTFields to anatomic structures that cannot be treated using transducer arrays positioned on the patient's skin (e.g., the spinal cord, which is surrounded by highly conductive cerebrospinal fluid that is in turn surrounded by the bony structure of the spine, both of which interfere with the penetration of TTFields into the spinal cord itself).

Note that in all of the embodiments described herein, it is important to include sensors for measuring temperature (such as thermistors) on or near the transducer arrays so that tissue temperature can be controlled and thermal damage to tissue avoided. In situations where a given transducer array is made up of a plurality of individual elements (e.g., ceramic discs) it is preferable to distribute a plurality of temperature sensors (e.g., thermistors) among the plurality of individual elements.

Figure 1:
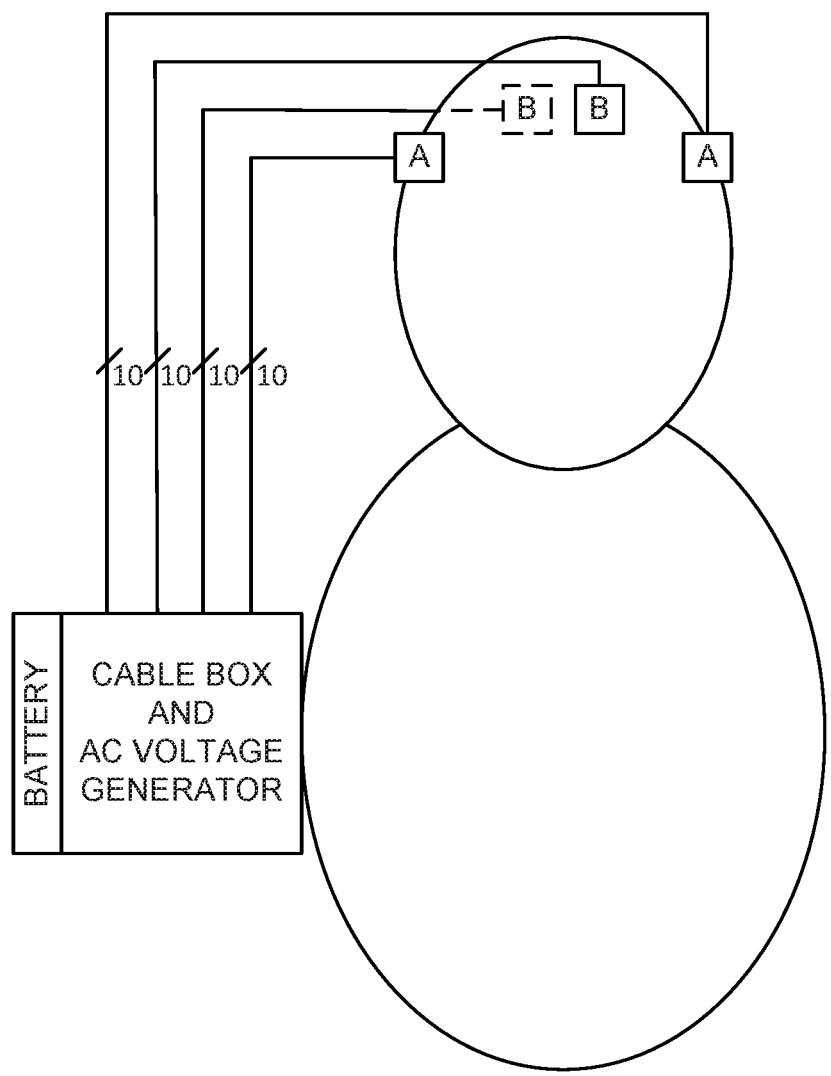
FIG. 1 is a block diagram of the prior art Optune® system that is used for delivering TTFields to a person's head.

One approach (not shown) for using implantable electrodes has a block diagram that is similar to the prior art FIG. 1 embodiment described above, except that the transducer arrays A, A, B, B are all implanted in the patient's body (e.g., between the scalp and the skull, or adjacent to the dura). While this approach enjoys advantages 1-8 listed above, it also suffers from a number of disadvantages. More specifically, each of the transducer arrays is connected to the cable box/AC voltage generator via a relatively long and bulky 10-conductor cable that extends outside of the body through a surgical incision or port (1 conductor for applying the AC voltage to the respective transducer array, plus 9 conductors that are used to obtain temperature readings from 8 different locations on the respective transducer array). The use of 10 conductor cables could make the system cumbersome. In addition, including a component that passes through the person's skin into the person's head raises the risk of acquiring an infection, which can be particularly problematic in the context of the brain.

Figure 2:
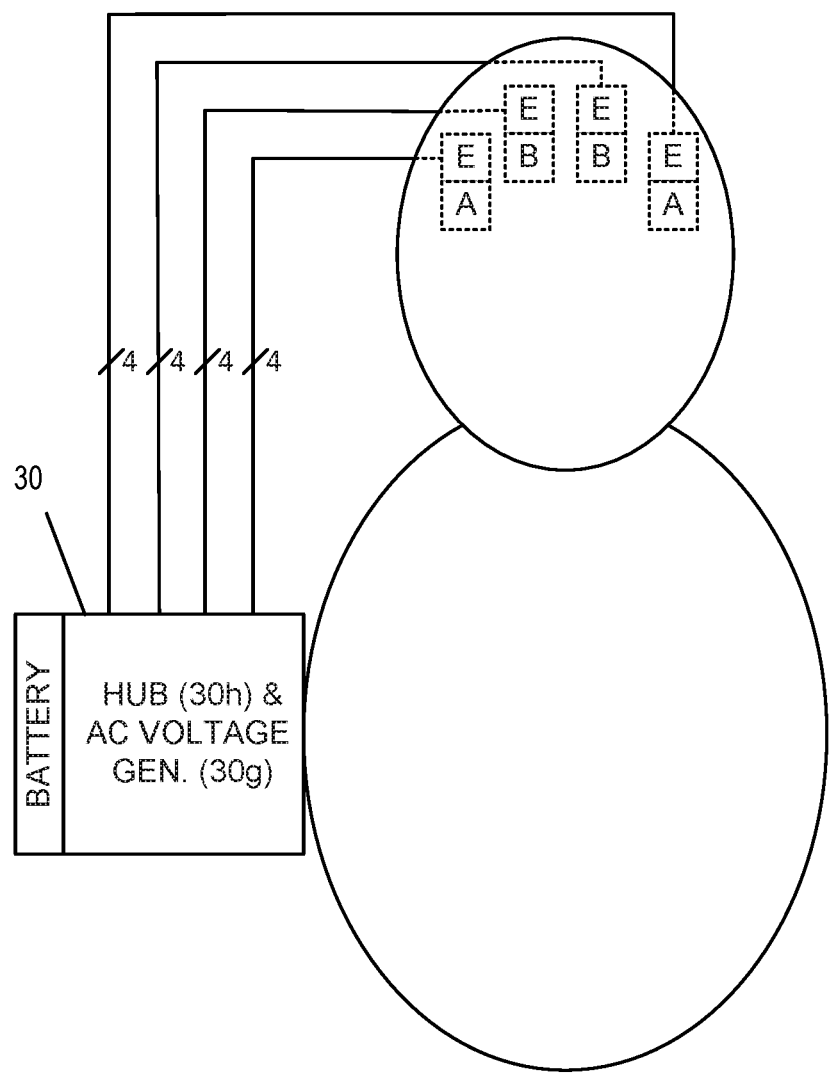
FIG. 2 is a block diagram of an embodiment that reduces the number of conductors in each cable that must pass through the patient's skin.

FIG. 2 depicts an improvement with respect to the approach described in the previous paragraph. In this approach, the number of conductors in each cable that must pass through the patient's skin is reduced from 10 to 4, which will significantly reduce the bulk and size of those cables. This may be accomplished, for example, by implanting additional electronics E adjacent to each of the implanted transducer arrays A, B and using a hub-based architecture. When the hub-based architecture is used, each of the electronic blocks E includes a multiplexor that reduces the number of conductors required for obtaining temperature measurements from 9 to 3, and a hub 30h is used to collect the temperature readings from each of the transducer arrays and forward those readings to the AC voltage generator 30g. The AC voltage generator 30g can then control the current that is applied to each of the transducer array pairs A/A, B/B in order to ensure that the transducer arrays do not overheat. Examples of circuitry that may be used to implement these electronic blocks E and the hub can be found in US 2018/0050200, entitled Temperature Measurement in Arrays for Delivering TTFields, which is incorporated herein by reference in its entirety. Note that while this embodiment does reduce the size and bulk of the wires that must pass through the person's skin, and provides advantages 1-8 listed above, it does not alleviate the risk of infection that is associated with a component that passes through the person's skin into the person's head.

Figure 3:
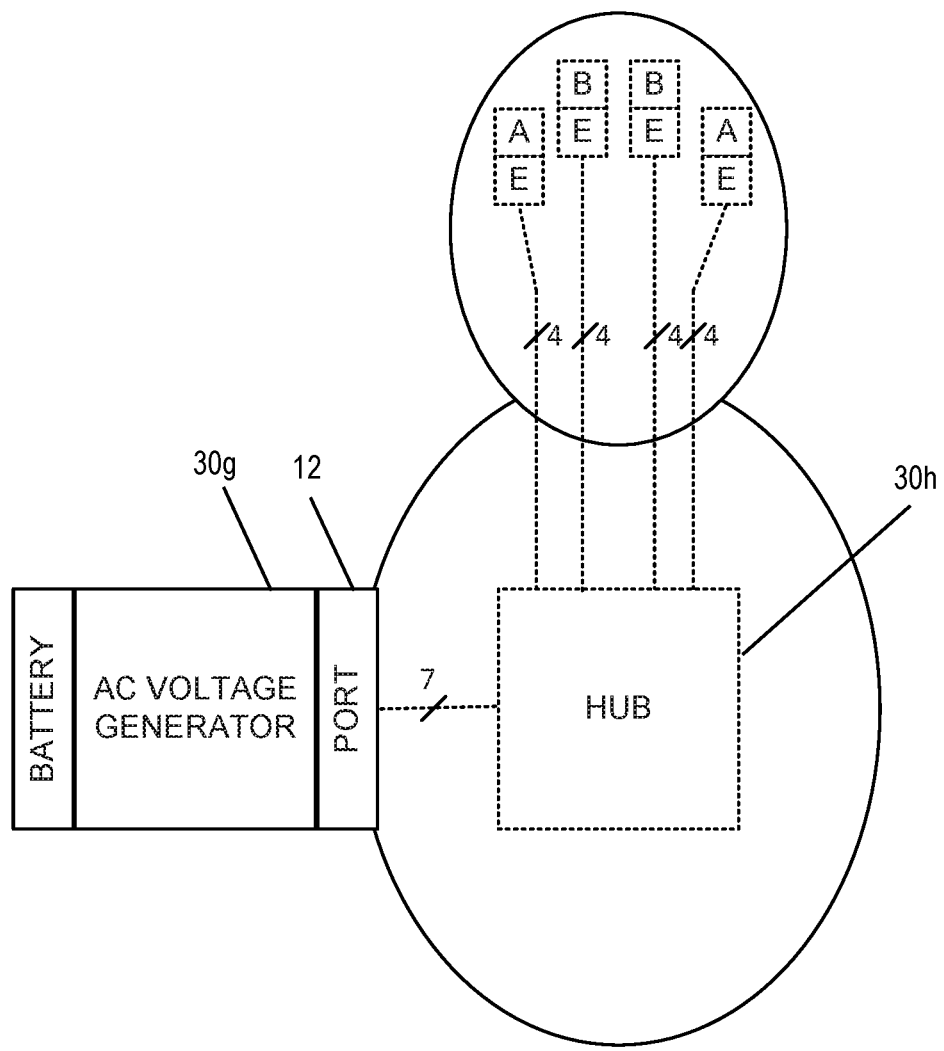
FIG. 3 is a block diagram of an embodiment in which both the transducer arrays and the hub are implanted in the patient's body.

FIG. 3 depicts a variation on the FIG. 2 approach. In the FIG. 3 embodiment, instead of positioning the hub outside the patient's body and running four cables through the patient's skin (as in FIG. 2), the electronics E, the transducer arrays A, B, and the hub 30h are implanted in the patient's body. In this FIG. 3 embodiment, only a single cable (i.e., the cable that runs between the hub 30h and the AC voltage generator 30g) must pass through the patient's skin. Optionally, this cable is connectorized using the depicted port 12. In the example depicted in FIG. 3, the hub 30h is positioned somewhere in the patient's thorax, and four 4-conductor cables run between the electronics E and the transducer arrays A, B in the patient's head and the hub 30h in the patient's thorax. This positioning is advantageous because there are no wires that pass directly from the outside world directly into the patient's head, thereby reducing the risk of a serious infection. But in variations of the FIG. 3 embodiment, the hub 30h may be positioned in the patient's head, in which case the port 12 that provides access would also be positioned in the patient's head.

In these FIG. 3 embodiments, the hub 30h collects temperature measurements from each of the transducer arrays A, B via the electronics E and forwards those temperature measurements to the AC voltage generator 30g via the port 12. The AC voltage generator 30g can then control the current that is applied to each of the transducer array pairs A/A, B/B in order to ensure that the transducer arrays do not overheat. This embodiment also provides advantages 1-8 listed above.

Figure 4:
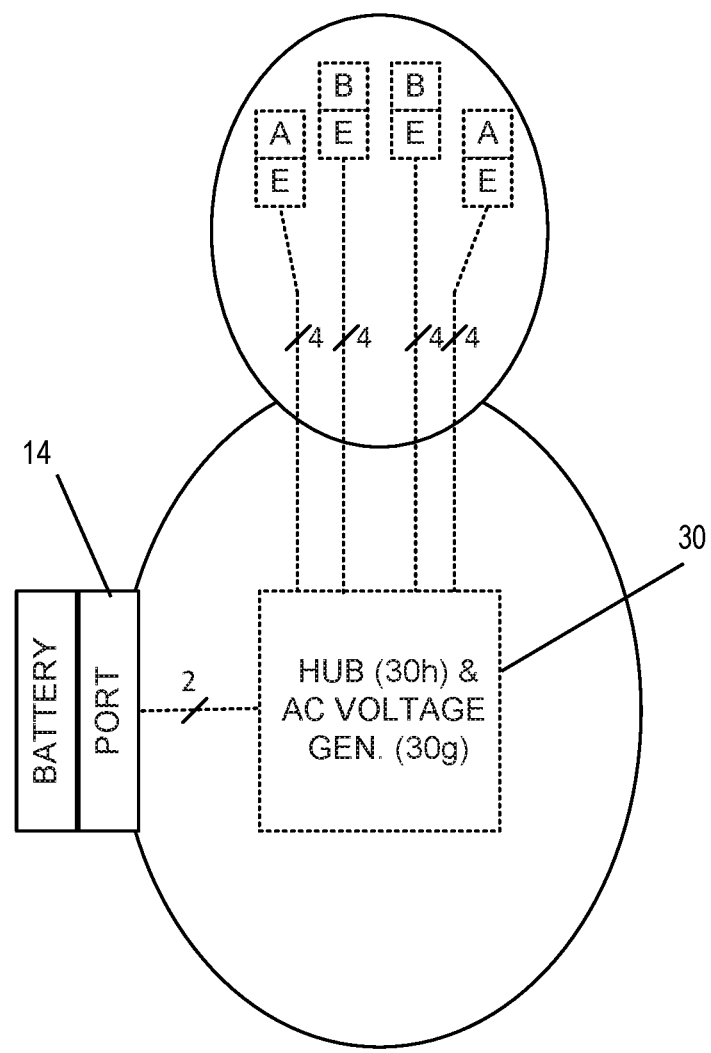
FIG. 4 depicts another approach that uses implantable electrodes in which the electrodes, the hub, and the AC voltage generator are all implanted within the patient's body.

FIG. 4 depicts another approach that uses implantable electrodes and also provides advantages 1-8 listed above. In this embodiment, the electrodes A, B, the hub 30h, and the AC voltage generator 30g are all implanted within the patient's body. Power for the hub 30h and the AC voltage generator 30g is provided via a port 14 that is positioned somewhere on the patient's skin (e.g. in the thorax). The power source (e.g. the battery) in this embodiment is external, and the battery provides power to the hub 30h and AC voltage generator 30g via the port. The port 14 is connected to the hub 30h and AC voltage generator 30g via appropriate wiring (e.g. a two conductor cable).

Since effective delivery of TTFields requires delivery of power on the order of 10-100 W, care must be taken to minimize heat dissipation in all embodiments where the AC voltage generator 30g is implanted within a patient's body (including this FIG. 4 embodiment). This is because any inefficiencies will lead to heating of tissue surrounding the field generator, which could lead to thermal damage of tissue in the patient's body. To accomplish this, the AC voltage generator 30g must operate with very high efficiency. One example of a circuit that is suitable for implementing a high efficiency AC voltage generator is described in U.S. Pat. No. 9,910,453, entitled High Voltage, High Efficiency Sine Wave Generator with Pre-Set Frequency and Adjustable Amplitude, which is incorporated herein by reference in its entirety.

The AC voltage generator 30g in these embodiments may optionally operate by starting with a low-voltage AC signal and amplifying and filtering that signal using circuitry integrating a transformer and LC filter. In some embodiments, an independent circuit combining the transformer and LC filter could be connected to each transducer array (or even to each element of each transducer array). In these embodiments, the low-voltage signal generator could be connected to each array (or element) via a wire placed remotely from the arrays. In this configuration, heat generated through losses within the system would be spread over a larger volume thereby reducing the risk of thermal damage to tissue, while enabling delivery of higher field intensities. To further reduce losses, the circuit on each array (or element) could be designed with a switch that switches the low voltage signal coming from the signal generator, thereby potentially reducing the losses within the system associated with switching at the arrays.

Optionally, the power source in the FIG. 4 embodiment may comprise multiple small batteries that are woven into a piece of clothing. This type of design would enable delivery of high power for extended periods of time while minimizing patient discomfort.

Figure 5:
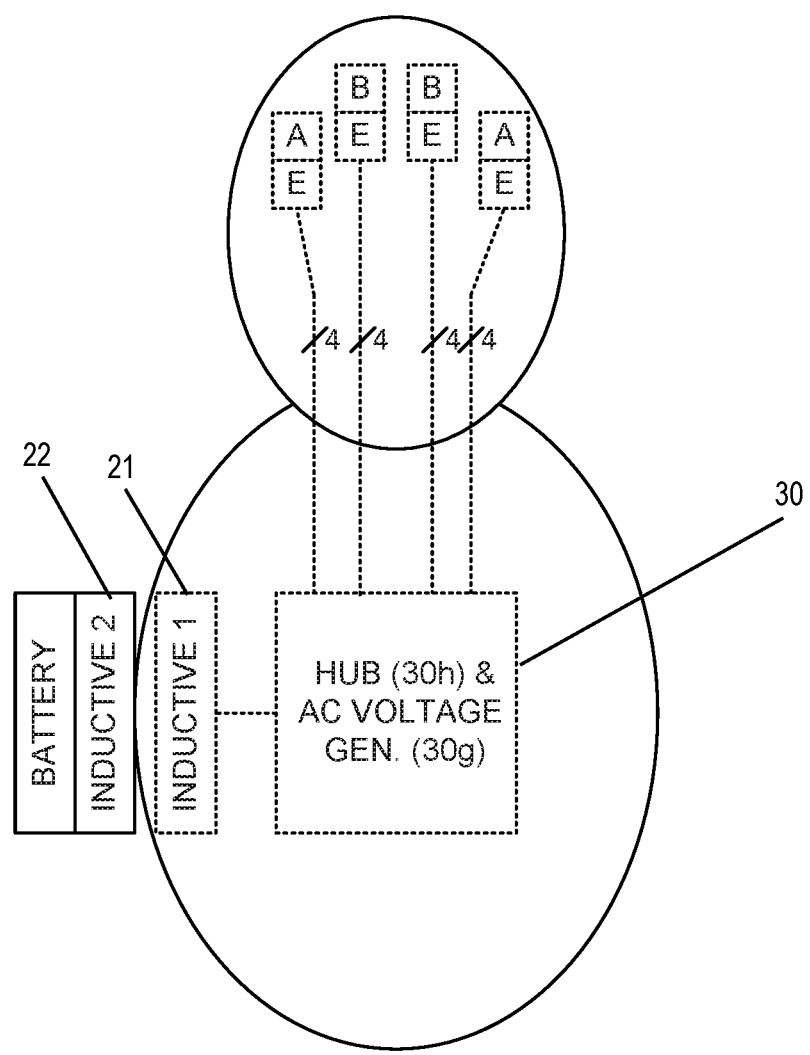
FIG. 5 depicts a variation on the FIG. 4 embodiment in which power is provided to the hub and the AC voltage generator using a wireless connection.

FIG. 5 depicts a variation on the FIG. 4 embodiments that also provides advantages 1-8 listed above. In the FIG. 5 embodiments, instead of providing power to the hub 30h and AC voltage generator 30g directly via a wired connection that passes from the outside world into the patient's body via a port 14 that is installed on the person's skin (as in FIG. 4), power in the FIG. 5 embodiment is provided to the hub 30h and the AC voltage generator 30g using a wireless connection. This may be accomplished, for example, by implanting a first circuit 21 inside the patient's body close to the patient's skin. The first circuit is configured to receive energy via inductive coupling. A second circuit 22 (which may optionally be powered by a battery and/or the AC main) is configured to transmit energy to the first circuit 21 via inductive coupling. The second circuit 22 is positioned outside the patient's body adjacent to the first circuit 21 during operation, so that energy can be inductively coupled from the second circuit 22 into the first circuit 21. The construction of these circuits 21, 22 for transmitting and receiving energy via inductive coupling are well known in the art and are commonly used, for example, for charging cell phones etc.

Optionally, the bulk and weight of the hardware that must be carried around by the patient can be advantageously reduced by providing multiple copies of the second circuit 22 at various locations that are frequented by the patient. For example, one copy of the second circuit 22 may be provided at the patient's office, a second copy of the second circuit 22 may be provided in the patient's car, a third copy of the second circuit 22 may be provided in the patient's living room, and a fourth copy of the second circuit 22 may be provided in or near the patient's bed. When multiple copies of the second circuit 22 are provided, the patient places the inductive coupling region of whichever second circuit 22 is nearby adjacent to the first circuit 21 implanted in their body so that the nearby second circuit 22 can power the implanted AC voltage generator 30g via inductive coupling. This arrangement can be particularly advantageous for people that move between various locations in a repeatable pattern (e.g., people who drive to work in the same car every day, work at the same desk every day, relax in the same living room every evening, and sleep in the same bed every night. Optionally, multiple copies of the second circuit 22 may be incorporated into a mattress so that the patient will not have to be hooked up to wires when they sleep, and can move around on the mattress.

Figure 6:
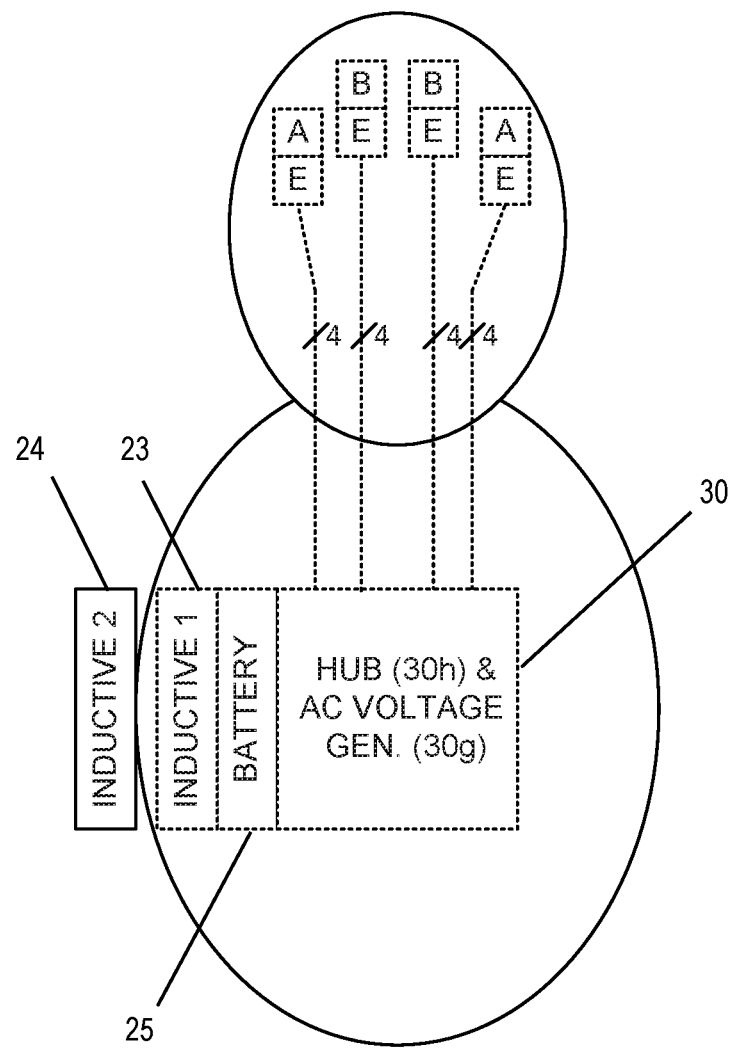
FIG. 6 depicts an embodiment that uses implanted electrodes that is powered by an implanted battery.

FIG. 6 depicts yet another embodiment that uses implanted electrodes and also provides advantages 1-8 listed above. Notably, the battery 25 in the FIG. 6 embodiment is implanted in the patient's body, and the implanted battery 25 is charged via induction. One challenge with this design is that the implanted battery 25 has to store relatively large amounts of energy. Thus, charging the battery 25 via induction may require the creation of large magnetic fluxes over extended periods of times. One method for overcoming this problem is a system in which a mattress incorporating a coil is used. The patient sleeps on this mattress, and the battery 25 powering the TTFields device is charged as the patient sleeps. In other embodiments, the coil could surround the bed.

Alternatively, a transcutaneous energy transfer system (see, e.g., Dissanayake et. al., IFMBE proceeding vol. 23) could be used to charge the implanted battery 25. In this case, a coil connected to a circuit designed to charge the implanted battery would be implanted transcutaneously. Charging would be performed with a separate device 24, which the patient would place close to the implanted coil 23. The external device could be fixed to the patient's body using a garment designed to fit tightly to the body, or using a medical adhesive. The patient would only be required to use the external charger when charging the implanted battery. This could occur for instance at night, while the patient is sleeping, thereby minimizing the need for the patient to carry an external device.

Optionally, the implanted transducer array elements may be configured to permit dynamic alteration of the field distribution in order to optimize delivery of TTFields. Unlike the situation with external transducer arrays, once the transducer arrays have been implanted it will be impractical to adjust the position of the transducer arrays in order to optimize the field distribution within the patient's body. A different approach for controlling the field distribution within the patient's body is therefore desirable when implantable arrays are used. One suitable approach for this purpose would be to implant transducer arrays with a relatively large number of switchable elements. The field can then be shaped by choosing subsets of array elements that are switched on when the field is delivered. As the tumor changes over time (response or progression), the field distribution could be changed by changing the array elements through which the field is generated.

Optionally, in any of the embodiments described above, the transducer arrays may be positioned on the dura. The advantage of this configuration is that power required to deliver TTFields to the brain would be reduced, because the field would not have to pass through the highly resistive layer of the skull. At the same time, this placement would reduce the need for invasive placement of the arrays in the brain-reducing the risk of damage to brain tissue and possibly the risk of infections. This configuration would also enable delivery of TTFields to large portions of the brain, as opposed to only delivering the TTFields to the tumor. In some cases, treating large portions of the brain may be advantageous. For instance, when treating the brain for metastases. In some embodiments, when treating regions of the body other than the head, the arrays could be placed subcutaneously to enable treatment of large regions. In other embodiments, the arrays could be placed in close proximity to the tumor. Placement in close proximity to the tumor would enable localized delivery of TTFields and reduce the power needed to deliver the fields.

In all of the embodiments described above, any component that is described as being implanted must be configured for implantation before it is actually implanted in a person's body. This means that it must be dimensioned to fit within the location where it will be implanted, and that all surfaces that might come into contact with tissue in the person's body must be biocompatible.

Optionally, in any of the embodiments described above, when the transducer arrays are implanted in the immediate vicinity of a tumor, the arrays could be made from or coated with a cytotoxic agent (e.g., platinum). Electrolysis caused by electric fields is expected to lead to release of platinum into the region around the tumor. Platinum is known to exert a cytotoxic effect on cancer cells, and therefore, release of platinum into the tumor may advantageously increase the anti-cancer effect of the TTFields treatment.

Optionally, in any of the embodiments described above, the transducer arrays A, B and the electronics E that are implanted into the patient's head may be designed as described below in connection with FIG. 7. The advantage of this configuration is that average field intensity can be maximized while minimizing the risk of heating by monitoring and adjusting the current to each electrode element in each transducer array independently, thereby improving the efficiency of TTFields delivery. These embodiments operate by alternately switching the current on and off for each individual electrode element that begins to overheat in order to reduce the average current for those electrode elements, without affecting the current that passes through the remaining electrode elements (which are not overheating).

Assume, for example, a situation in which 500 mA of current is passing through a transducer array that includes 10 electrode elements, and only a single one of those electrode elements begins to overheat. Assume further that a 10% reduction of current through the single electrode element would be necessary to prevent that single electrode element from overheating. The embodiments described herein can cut the average current through the single electrode element by 10% by switching the current through that single electrode element on and off with a 90% duty cycle, while leaving the current on full-time for all the remaining electrode elements. Note that the switching rate must be sufficiently fast so that the instantaneous temperature at the single electrode element is never too hot, in view of the thermal inertia of the electrode elements. For example, a 90% duty cycle could be achieved by switching the current on for 90 ms and switching the current off for 10 ms. In some preferred embodiments, the period of switching the current on and off is less than 1 s.

When this approach is used, the current through the remaining 9 electrode elements can remain unchanged (i.e., 50 mA per electrode element), and only the current through the single electrode element is reduced to an average of 45 mA. The average net total current through the transducer array will then be 495 mA (i.e., 9×50+45), which means that significantly more current can be coupled into the person's body without overheating at any of the electrode elements.

The system may even be configured to increase the current through the remaining nine electrode elements in order to compensate for the reduction in current through the single electrode element. For example, the current through the remaining nine electrode elements could be increased to 50.5 mA per electrode element (e.g., by sending a request to the AC voltage generator to increase the voltage by 1%). If this solution is implemented, the average net total current through the entire transducer array would be (9 electrodes× 50.5 mA+1 electrode×50.5 mA×0.9 duty cycle)=499.95 mA, which is extremely close to the original 500 mA of current.

If, at some subsequent time (or even at the same time), the temperature at a second electrode element begins to overheat, a similar technique (i.e. a reduction in the duty cycle from 100% to something less than 100%) may be used to prevent the second electrode element from overheating.

In some embodiments, this technique may be used to individually customize the duty cycle at each of the electrode elements in order to maximize the current that flows through each of those electrode elements without overheating. Optionally, instead of taking remedial action to reduce the duty cycle only when a given electrode element begins to overheat, the system may be configured to proactively set the duty cycle at each of the electrode elements in a given transducer array individually so as to equalize the temperature across all of the electrode elements in the array. For example, the system could be configured to individually set the duty cycle at each electrode element so as to maintain a temperature that hovers around a set temperature at each of the electrode elements. Optionally, the system may be configured to send a request to the AC voltage generator to increase or decrease the voltage as required in order to achieve this result.

This approach can be used to ensure that each and every electrode element will carry the maximum average current possible (without overheating), which will provide an increased field strength in the tumor and a corresponding improvement in the treatment.

Figure 7:
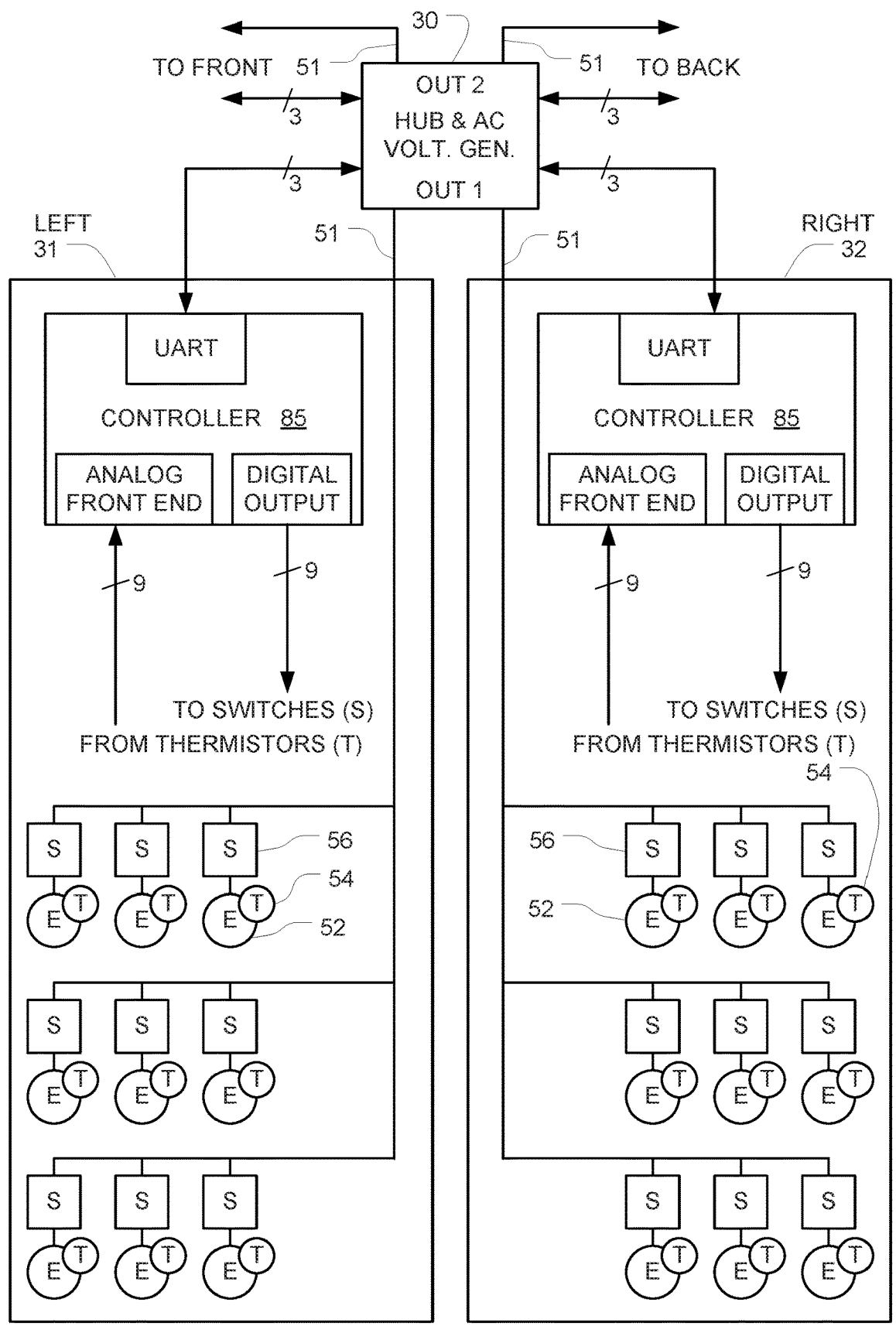
FIG. 7 depicts an embodiment that can switch the current to each individual electrode element on or off based on the state of a set of electrically controlled switches.

FIG. 7 depicts an embodiment that periodically switches the current on and off for each individual electrode element that begins to overheat. The hub/AC voltage generator 30 has two outputs (OUT1 and OUT2), each of which has two terminals. The hub/AC voltage generator 30 generates an AC signal (e.g. a 200 kHz sine wave) between the two terminals of each of those outputs in an alternating sequence (e.g., activating OUT1 for 1 sec., then activating OUT2 for 1 sec., in an alternating sequence). A pair of conductors 51 are connected to the two terminals of OUT1, and each of those conductors 51 goes to a respective one of the left and right transducer assemblies 31, 32. Each of these transducer assemblies includes a plurality of electrode elements 52 (which collectively correspond to the transducer arrays A, B in FIGS. 2-6) and electronic components 56, 85 (which correspond to the electronics E in FIGS. 2-6). A second pair of conductors 51 are connected to the two terminals of OUT2 and each of those conductors 51 goes to a respective one of the front and back transducer assemblies (not shown). The construction and operation of the front and back transducer assemblies is similar to the construction of the left and right transducer assemblies 31, 32 depicted in FIG. 7.

Each of the transducer assemblies 31, 32 includes a plurality of electrode elements 52. In some preferred embodiments, each of these electrode elements 52 is a capacitively coupled electrode element. However, in this FIG. 7 embodiment, instead of wiring all of the electrode elements 52 in parallel, an electrically controlled switch (S) 56 is wired in series with each electrode element (E) 52, and all of these S+E combinations 56+52 are wired in parallel. Each of the switches 56 is configured to switch on or off independently of other switches based on a state of a respective control input that arrives from the digital output of the respective controller 85. When a given one of the switches 56 is on (in response to a first state of the respective control input), current can flow between the electrical conductor 51 and the respective electrode element 52. Conversely, when a given one of the switches 56 is off (in response to a second state of the respective control input), current cannot flow between the electrical conductor 51 and the respective electrode element 52.

In some preferred embodiments, each of the capacitively coupled electrode elements 52 is disc-shaped and has a dielectric layer on one side.

In some preferred embodiments, each of the capacitively coupled electrode elements 52 comprises a conductive plate with a flat face, and the dielectric layer is disposed on the flat face of the conductive plate. In some preferred embodiments, all of the capacitively coupled electrode elements are held in place by a support structure. In some preferred embodiments, the electrical connection to each of the electrode elements 52 comprises a trace on a flex circuit.

Each of the transducer assemblies 31, 32 also includes a temperature sensor 54 (e.g., a thermistor) positioned at each of the electrode elements 52 so that each temperature sensor 54 can sense the temperature of a respective electrode element 52. Each of the temperature sensors 54 generates a signal indicative of the temperature at (e.g., beneath) the respective electrode element 52. The signals from the temperature sensors 54 are provided to the analog front and of the respective controller 85.

In embodiments where thermistors are used as the temperature sensors 54, temperature readings may be obtained by routing a known current through each thermistor and measuring the voltage that appears across each thermistor. In some embodiments, thermistor-based temperature measurements may be implemented using a bidirectional analog multiplexer to select each of the thermistors in turn, with a current source that generates a known current (e.g., 150 µA) positioned behind the multiplexer, so that the known current will be routed into whichever thermistor is selected by the analog multiplexer at any given instant. The known current will cause a voltage to appear across the selected thermistor, and the temperature of the selected thermistor can be determined by measuring this voltage. The controller 85 runs a program that selects each of the thermistors in turn and measures the voltage that appears across each of the thermistors (which is indicative of the temperature at the selected thermistor) in turn. An example of suitable hardware and procedures that may be used to obtain temperature readings from each of the thermistors is described in US 2018/0050200, which is incorporated herein by reference in its entirety.

In some preferred embodiments, the controller 85 may be implemented using a single-chip microcontroller or Programmable System on Chip (PSoC) with a built in analog front end and multiplexer. Suitable part numbers for this purpose include the CY8C4124LQI-443. In alternative embodiments, other microcontrollers may be used with either built-in or discrete analog front ends and multiplexers, as will be apparent to persons skilled in the relevant arts.

In alternative embodiments, not shown, an alternative approach (e.g., the conventional voltage divider approach) for interfacing with the thermistors may be used in place of the constant current approach described above. In other alternative embodiments, a different type of temperature sensor may be used in place of the thermistors described above. Examples include thermocouples, RTDs, and integrated circuit temperature sensors such as the Analog Devices AD590 and the Texas Instruments LM135. Of course, when any of these alternative temperature sensors is used, appropriate modifications to the circuit (which will be apparent to persons skilled in the relevant arts) will be required.

In some embodiments, the controller 85 is programmed to keep the temperature at all of the electrode elements below a safety threshold using intelligence that is built into each transducer assembly 31. This may be accomplished, for example, by programming the controller 85 to start out by setting its digital output so that each of the switches 56 is continuously on (i.e., with a 100% duty cycle). Then, based on signals arriving via the controller 85 analog front end, the controller 85 determines whether the temperature at each of the electrode elements exceeds an upper threshold that is below the safety threshold. When the controller 85 detects this condition, the controller 85 reduces the duty cycle for the corresponding switch 56 by toggling the corresponding digital output at the desired duty cycle. This will interrupt the current to the corresponding electrode element 52 at the same duty cycle, thereby reducing the average current at the specific electrode elements 52 whose temperature exceeds that upper threshold. The level of reduction in current is determined by the duty cycle. For example, using a 50% duty cycle will cut the current by half; and using a 75% duty cycle will cut the current by 25%.

Notably, this procedure only interrupts the current to specific ones of the electrode elements 52 on the transducer assembly 31, and does not interrupt the current to the remaining electrode elements 52 on that transducer assembly 31. This eliminates or reduces the need to cut the current that is being routed through the electrode elements when only a small number of those electrode elements are getting hot.

A numeric example will be useful to illustrate this point. Assume, in the FIG. 7 embodiment, that the left and right transducer assemblies 31, 32 are implanted on the left and right sides of a subject's head, respectively; that all of the switches 56 in the transducer assemblies 31, 32 are in the ON state with a 100% duty cycle; and that the hub/AC voltage generator 30 is initially outputting 500 mA of current into the conductors 51. An AC voltage will appear between the electrode elements 52 of the left transducer assembly 31 and the electrode elements 52 of the right transducer assembly 32, and the 500 mA AC current will be capacitively coupled through the electrode elements 52 through the subject's head. The controller 85 in each of the transducer assemblies 31, 32 monitors the temperature at each of the electrode elements 52 in that transducer assembly by inputting signals from each of the temperature sensors 54 via the analog front end of the controller 85. Now assume that a given one of the electrode elements 52 in the transducer assembly 31 begins to overheat. This condition will be reported to the controller 85 in the transducer assembly 31 via a signal from the corresponding temperature sensor 54. When the controller 85 recognizes that the given electrode element 52 is overheating, the controller 85 will toggle the control signal that goes to the corresponding switch 56 at the desired duty cycle in order to periodically interrupt the current to the given electrode element 52 and maintain a lower average current.

Note that if the duty cycle at only one of the remaining electrode elements 52 is being reduced, it may be possible to maintain the original 500 mA current (and enjoy the advantages that arise from using the full current). However, if the duty cycle at a large enough number of the electrode elements 52 is being reduced, the original 500 mA current may have to be dropped. To accomplish this, the controller 85 can send a request to the hub/AC voltage generator 30 via the UART in the controller 85. When the hub/AC voltage generator 30 receives this request, the hub/AC voltage generator 30 will reduce the output current at its corresponding output OUT1.

Optionally, the duty cycle that is selected by the controller 85 may be controlled based on the speed at which the given electrode element 52 heats up after current is applied to the given electrode element 52 (as measured via the temperature sensors 54 and the analog front end of the controller 85). More specifically, if the controller 85 recognizes that a given electrode element 52 is heating up twice as fast as expected, the controller 85 can select a duty cycle of 50% for that electrode element. Similarly, if the controller 85 recognizes that a given electrode element 52 is heating up 10% faster than expected, the controller 85 can select a duty cycle of 90% for that electrode element.

In other embodiments, instead of deterministically cutting the average current by reducing the duty cycle, the controller 85 can reduce the average current at a given electrode element 52 based on real-time temperature measurements by turning off the current to the given electrode element 52 and waiting until temperature measured using the temperature sensors 54 drops below a second temperature threshold. Once the temperature drops below this second temperature threshold, the controller 85 can restore the current to the given electrode element 52. This may be accomplished, for example, by controlling the state of the control input to the switch 56 that was previously turned off so that the switch 56 reverts to the ON state, which will allow current to flow between the electrical conductor and the respective electrode element 52. In these embodiments, the current to a given electrode element 52 may be repeatedly switched off and on based on real-time temperature measurements in order to keep the temperature at the given electrode element 52 below the safety threshold.

In the FIG. 7 embodiment, each of the transducer assemblies 31, 32 is connected to the hub/AC voltage generator 30 via a respective cable. Notably only 4 conductors are required in each of the cables that run between the transducer assembly and the hub/AC voltage generator 30 (i.e., Vcc, data, and ground for implementing serial data communication, plus one additional conductor 51 for the AC current TTFields signal).

Note that in FIG. 7, each transducer assembly 31, 32 includes nine electrode elements 52, nine switches 56, and nine temperature sensors 54. But in alternative embodiments, each transducer assembly 31, 32 can include a different number (e.g., between 8 and 25) of electrode elements 52 and a corresponding number of switches and temperature sensors.

In these embodiments, the decision to adjust the duty cycle or turn off one or more of the switches 56 in a given transducer assembly 31, 32 in order to reduce the average current to one or more of the electrode elements 52 is made locally in each transducer assembly 31, 32 by the controller 85 within that transducer assembly 31, 32. But in alternative embodiments, the decision to adjust the duty cycle or turn off one or more of the switches 56 may be made by the hub/AC voltage generator 30 (or another remote device). In these embodiments, the controller 85 in each of the transducer assemblies 31, 32 obtains the temperature readings from each of the temperature sensors 54 in the respective transducer assembly and transmits those temperature readings to the hub/AC voltage generator 30 via the UART of the controller 85. The hub/AC voltage generator 30 decides which, if any, of the switches require a duty cycle adjustment or should be turned off based on the temperature readings that it received, and transmits a corresponding command to the corresponding controller 85 in the corresponding transducer assembly 31, 32. When the controller 85 receives this command from the hub/AC voltage generator 30, the controller 85 responds by setting its digital output to a state that will switch off the corresponding switch 56 at the appropriate times, in order to carry out the command that was issued by the hub/AC voltage generator 30. In these embodiments, the hub/AC voltage generator 30 can also be programmed to reduce its output current if a reduction in current is necessary to keep the temperature at each of the electrode elements 52 below the safety threshold.

In these embodiments, the controller 85 may be programmed to operate as a slave to a master controller located in the hub/AC voltage generator 30. In these embodiments, the controller 85 starts out in a quiescent state, where all it does is monitor incoming commands from the master controller that arrive via the UART. Examples of commands that can arrive from the master controller include a "collect temperature data" command, a "send temperature data" command, and a "set switches" command. When the controller 85 recognizes that a "collect temperature data" command has arrived, the controller 85 will obtain temperature readings from each of the temperature sensors 54 and store the result in a buffer. When the controller 85 recognizes that a "send temperature data" command has arrived, the controller 85 will execute a procedure that transmits the previously collected temperature readings from the buffer to the hub/AC voltage generator 30 via the UART 86. And when the controller 85 recognizes that a "set switches" command has arrived, the controller 85 will execute a procedure to output appropriate voltages on its digital output in order to set each of the switches 56 to a desired state (i.e., either ON, OFF, or switching between on and off at a commanded duty cycle) based on data that arrives from the hub/AC voltage generator 30.

In the embodiments described above, a single controller 85 is used in each of the transducer assemblies 31, 32 to control the switches 56 in that assembly and also to obtain temperature measurements from each of the temperature sensors 54 in that assembly. In alternative embodiments, instead of using a single controller 85 to control the switches 56 and to obtain the temperature measurements, those two tasks may be divided between two controllers, one of which is only used to control the switches 56, and the other of which is used to obtain the temperature measurements from each of the temperature sensors 54 (e.g., using any of the approaches described above). In these embodiments, these two controllers may communicate directly with each other, and/or the hub/AC voltage generator 30.

In other alternative embodiments (not shown), temperature measurement does not rely on a local controller that is positioned in the vicinity of the electrode elements 52. Instead, wires run from each of the temperature sensors 54 back to the hub/AC voltage generator 30, and the hub/AC voltage generator uses signals that arrive via these wires to determine the temperature at each of the temperature sensors 54.

Figure 8:
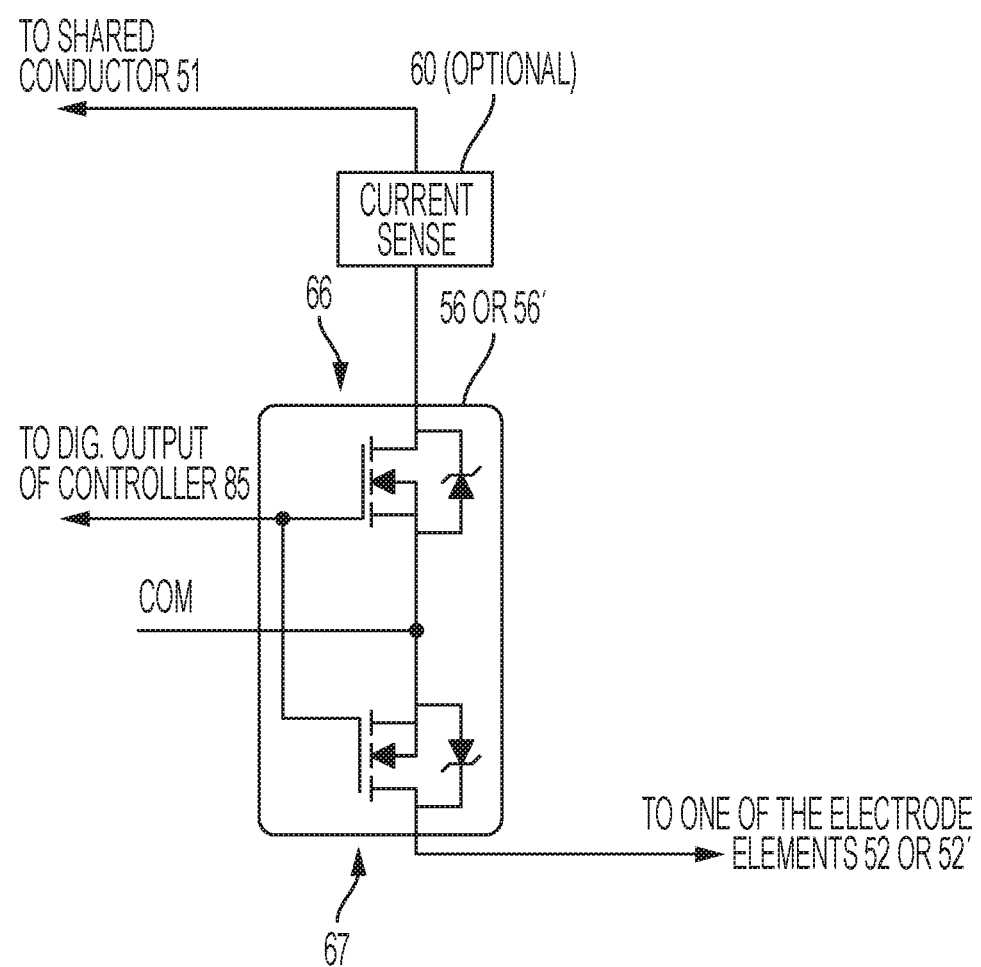
FIG. 8 is a schematic diagram of a circuit that is suitable for implementing the switches in the FIG. 7 embodiment.

FIG. 8 is a schematic diagram of a circuit that is suitable for implementing the switches 56, 56' in the FIG. 7 embodiment described above. The circuit includes two field effect transistors 66, 67 wired in series, which is a configuration that can pass current in either direction. One example of a suitable FET for this circuit is the BSC320N20NSE. (Note that the diodes depicted in FIG. 8 are inherently included within the FETs 66, 67 themselves.) The series combination of the two FETs 66, 67 will either conduct or block the flow of electricity, depending on the state of the control input that arrives from one of the digital outputs of the controller 85 described above. When the series combination is conducting, current can flow between the shared conductor 51 and the respective electrode element 52, 52'. On the other hand, when the series combination of FETs 66, 67 is not conducting, current will not flow between the shared conductor 51 and the respective electrode element 52, 52'.

Optionally, a current sensing circuit 60 may be positioned in series with the switch 56, 56'. The current sensing circuit 60 may be implemented using any of a variety of conventional approaches that will be apparent to persons skilled in the relevant arts. When the current sensing circuit 60 is included, it generates an output that is representative of the current, and this output is reported back to the controller 85 (shown in FIG. 7). The controller 85 can then use this information to determine whether the measured current is as expected and take appropriate action if necessary. For example, if an overcurrent condition is detected, the controller 85 can turn off the corresponding switch. Of course, in those embodiments where the current sensing circuit 60 is omitted, it should be replaced with the wire (or other conductor) so that the current can flow between the shared conductor 51 and the top leg of the upper FET 60.

In the illustrated embodiment, the current sensing circuit 60 is positioned between the shared conductor 51 and the top leg of the upper FET 60. But in alternative embodiments, the current sensing circuit may be positioned between the bottom leg of the lower FET 67 and the respective electrode element 52, 52'. And in other alternative embodiments (not shown), the current sensing circuit may be integrated within the circuitry of the switch itself.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for delivering tumor treating fields, the apparatus comprising:
 a plurality of sets of electrode elements that are configured to impose tumor treating fields in a treatment area of a person's body, wherein each of the sets of electrode elements is configured for implantation within the person's body;
 a plurality of temperature sensors configured for implantation within the person's body and positioned with respect to the sets of electrode elements to measure a temperature at each of the sets of electrode elements;

a circuit configured for implantation within the person's body configured for collecting temperature measurements from the plurality of temperature sensors; and an AC voltage generator configured for implantation within the person's body and configured to apply an AC voltage across the plurality of sets of electrode elements and control a current that is applied to the plurality of sets of electrode elements based on signals from the plurality of temperature sensors so that the electrode elements do not overheat.

2. The apparatus of claim 1, further comprising an inductively coupled circuit configured for implantation within the person's body and configured to power the AC voltage generator.

3. The apparatus of claim 1, further comprising a battery configured for implantation within the person's body and configured to power the AC voltage generator.

4. The apparatus of claim 3, further comprising an inductively coupled circuit configured for implantation within the person's body and configured to charge the battery.

5. The apparatus of claim 1, wherein each of the sets of electrode elements comprises a plurality of capacitively coupled electrode elements, and wherein each of the electrode elements comprises a conductive plate with a flat face, with a dielectric layer disposed on the flat face of the conductive plate.

6. The apparatus of claim 5, wherein each of the capacitively coupled electrode elements comprises a ceramic disc.

7. The apparatus of claim 1, wherein each of the temperature sensors comprises a thermistor.

8. The apparatus of claim 1, wherein the plurality of sets of electrode elements, the plurality of temperature sensors, the circuit, and the AC voltage generator are all implanted in the person's body.

9. An apparatus for delivering tumor treating fields, the apparatus comprising:
a plurality of sets of electrode elements that are configured to impose tumor treating fields in a treatment area of a person's body, wherein each of the sets of electrode elements is configured for implantation within the person's body;
a plurality of temperature sensors configured for implantation within the person's body and positioned to measure a temperature at each of the sets of electrode elements;
an AC voltage generator configured for implantation within the person's body and configured to apply an AC voltage across the plurality of sets of electrode elements and control a current that is applied to the plurality of sets of electrode elements based on signals from the plurality of temperature sensors so that the electrode elements do not overheat.

10. The apparatus of claim 9, further comprising an inductively coupled circuit configured for implantation within the person's body and configured to power the AC voltage generator.

11. The apparatus of claim 9, further comprising a battery configured for implantation within the person's body and configured to power the AC voltage generator.

12. The apparatus of claim 11, further comprising an inductively coupled circuit configured for implantation within the person's body and configured to charge the battery.

13. The apparatus of claim 9, wherein each of the sets of electrode elements comprises a plurality of capacitively coupled electrode elements, and wherein each of the electrode elements comprises a conductive plate with a flat face, with a dielectric layer disposed on the flat face of the conductive plate.

14. The apparatus of claim 13, wherein each of the capacitively coupled electrode elements comprises a ceramic disc.

15. The apparatus of claim 9, wherein each of the temperature sensors comprises a thermistor.

16. The apparatus of claim 9, wherein the plurality of sets of electrode elements, the plurality of temperature sensors, and the AC voltage generator are all implanted in the person's body.

17. The apparatus of claim 1, wherein one or more electrode element in each set of electrode elements has a temperature sensor associated with it.

18. The apparatus of claim 1, wherein each electrode element in each set of electrode elements has a temperature sensor associated with it.

19. The apparatus of claim 9, wherein one or more electrode element in each set of electrode elements has a temperature sensor associated with it.

20. The apparatus of claim 9, wherein each electrode element in each set of electrode elements has a temperature sensor associated with it.

21. The apparatus of claim 17, wherein the AC voltage generator is configured to control a current that is applied to each individual electrode element based on signals from the plurality of temperature sensors so that the electrode elements do not overheat.

22. The apparatus of claim 19, wherein the AC voltage generator is configured to control a current that is applied to each individual electrode element based on signals from the plurality of temperature sensors so that the electrode elements do not overheat.

* * * * *